US006859282B1

(12) United States Patent
Weber et al.

(10) Patent No.: US 6,859,282 B1
(45) Date of Patent: Feb. 22, 2005

(54) OPTICAL PROBE FOR DETERMINING THE FAT/LEAN INTERFACE IN CUTS OF MEAT

(75) Inventors: Thomas M. Weber, McLean, VA (US); Diane S. Callow, Albuquerque, NM (US); James F. Jones, Albuquerque, NM (US); Michael A. Kuehl, Alburquerque, NM (US); Barry L. Spletzer, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 258 days.

(21) Appl. No.: 10/040,684

(22) Filed: Jan. 4, 2002

(51) Int. Cl.$^7$ .................... G01M 33/12; G01N 21/49
(52) U.S. Cl. ........................ 356/446; 356/630
(58) Field of Search ................ 356/445–448, 356/630

(56) References Cited

U.S. PATENT DOCUMENTS

| | | | |
|---|---|---|---|
| 3,224,320 A | * 12/1965 | Knudsen | 356/445 |
| 4,078,313 A | 3/1978 | Hennessy | |
| 4,209,878 A | 7/1980 | Albert | |
| 4,246,837 A | 1/1981 | Chenery | |
| 4,270,274 A | * 6/1981 | Hennessy | 356/630 |
| 4,439,037 A | * 3/1984 | Northeved et al. | 356/445 |
| 4,622,974 A | * 11/1986 | Coleman et al. | 600/342 |
| 4,825,711 A | 5/1989 | Jensen | |
| 4,884,891 A | * 12/1989 | Borsboom | 356/446 |
| 6,088,114 A | * 7/2000 | Richmond et al. | 356/417 |
| 6,118,542 A | * 9/2000 | Andersen et al. | 356/445 |
| 6,277,019 B1 | 8/2001 | Veldkamp et al. | |
| 6,563,580 B1 | * 5/2003 | Aignel et al. | 356/300 |

OTHER PUBLICATIONS

Swatland, H.J., "Effect of Connective Tissue on the Shape of Reflectance Spectra Obtained with a Fibre-Optic Fat-Depth Probew in Beef," *Meat Science*, vol. 57, pp. 209-213 (2001).

* cited by examiner

Primary Examiner—Richard A. Rosenberger
(74) Attorney, Agent, or Firm—Peacock, Myers and Adams, P.C.

(57) ABSTRACT

An apparatus and method for locating the boundary surface between a layer of fatty tissue and lean tissue in a cut of meat, such as beef, such as slabs of meat undergoing trimming and cutting in commercial meet processing facilitates. The invention exploits the fact that fatty tissue and lean tissue have significantly different responses to incident light energy. By gauging the degree to which a generated beam of light is scattered and reflected by the tissues under evaluation, the invention permits the character of the tissue to be ascertained. An incident beam of light, such as green light, is generated and transmitted to a probe tip, which tip is inserted into the cut of meat under investigation. The light beam is emitted into the meat tissues from the probe tip, and then is scattered and reflected by the tissues, whereupon some fraction of the emitted light returns to the probe tip. The returning light energy is transmitted to a detector; relative changes in the returning light transmitted to the detector permit the operator to determine when the probe tip is approaching or penetrating the fat/lean tissue interface.

18 Claims, 4 Drawing Sheets

OPTICAL PROBE FOR DETERMINING THE FAT/LEAN INTERFACE IN CUTS OF MEAT

The Government has rights to this invention pursuant to Contract No. DE-AC04-94AL85000 awarded by the U.S. Department of Energy, and also certain rights pursuant to Cooperative Research and Development Agreement No. SC96/01455, Sandia National Laboratories.

BACKGROUND OF THE INVENTION

1. Field of the Invention (Technical Field)

The present invention relates to meat cutting, such as commercial beef cutting, and in particular to an optical probe for automating meat cutting, and specifically to an optical probe for determining the location of the interface between fat material and lean material in a cut of meat.

2. Background Art

Note that the following discussion refers to a number of publications by author(s) and year of publication, and that due to their recent publication dates certain publications are not to be considered as prior art vis-a-vis the present invention. Discussion of such publications herein is given for more complete background and is not to be construed as an admission that such publications are prior art for patentability determination purposes.

In the process of cutting and trimming meats for sale, it is desirable to ascertain the location of the interface between an upper layer of fatty tissue and the underlying lean meat, in order to trim away a desired quantity of fat. These processes can be difficult to perform efficiently, especially in high-volume commercial meat processing facilities. It has been necessary in the past to make an incision into the fat, insert a measuring device therein, and view a scale through the device which indicates fat thickness. The scale is often difficult to read and often the measurement is taken while the carcass is moving down the processing line, leading to a tendency to conduct the measurement in an incomplete manner.

To separate the lean meat from the fatty tissue, it is necessary to determine the interface between the fatty tissue and lean meat tissue ("fat/lean interface") in the meat carcass. Knowledge of the location of the fat/lean interface aids in the process of trimming a selected amount of fatty tissue from the meat carcass, for example to produce a cut of meat with a selected thickness of fat that is uniformly distributed across the product. Currently, where human workers manually trim the fat from the carcass—which is still generally the norm, even in industrialized nations—they are constantly "poking" the carcass, feeling for the tough membrane that marks the interface, thereby gauging fat thickness. Human tactile estimations of the location of the interface are less than desirable in a variety of ways. Additionally, the location of the fat/lean interface must be known to realize any benefits from an automated trimming operation.

Various mechanisms have been developed to address the need of determining the fat thickness on a meat carcass, and include those described in U.S. Pat. No. 4,078,313 to Hennessy, entitled "Measuring Device," and U.S. Pat. No. 4,209,878 to Albert, entitled "Automatic Meat Inspecting and Trimming Machine and Method." The Hennessy patent discusses a device where light is emitted into the meat tissue and reflected light is detected by a center element located within the probe. The size of the Hennessy device and the internal circuitry enclosed within the handle makes it cumbersome to use, and the device tends to mar the meat in the course of taking the measurement. Albert discusses a set of pneumatically operated probes for sensing fat thickness in a meat product, but does not disclose the use of light to detect lean meat or fatty tissue.

Also of note are U.S. Pat. No. 4,246,837 to Chenery, entitled "Meat Cutting Apparatus," and U.S. Pat. No. 4,825,711 to Jensen et al., entitled "Probe Unit for Automatic Determination of Quality Properties of Meat." The Chenery patent uses a row of needle probes that are pushed into the meat carcass and sense a change in electrical conductivity between the lean and fat portions in order to determine the fat/lean interface within the meat. Jensen uses a light reflection meter at one end of a meat probe to detect light reflected from the tissue and to determine the type and quality of tissue being penetrated. The light reflector comprises a light diode and photodiode that are secured directly within the probe. Conventional electrical wiring is used to provide energy to the light diode and to receive an amplified signal from the photodiode. U.S. Pat. No. 6,088,114 to Richmond et al., entitled "Apparatus for Use in Determining Meat Tenderness" also provides background information. The use of fiber optics in a fat depth probe is described in an article by H. J. Swatland, entitled "Effect of Connective Tissue on the Shape of Reflectance Spectra Obtained with a Fibre-Optic Fat-Depth Probe in Beef," Meat Science 57, 2001, pgs. 209–213.

Limitations in these prior art devices include the cumbersome size of the devices and the tendency to leave permanent markings in the meat that is probed, as well as inefficiencies in determining the fat/lean interface. It would be useful if a probe could be designed to be of a very small diameter, on the order of 0.125 inches in diameter, so that the probe can be inserted into the meat sample with minimal damage to the meat. It would also be beneficial to have a device wherein green light can be emitted into the meat sample as fatty tissue and lean meat tissue absorb green light differently. It would also be advantageous for such a device to have the green light source as well as the light detector for return light from the tissue located remotely from the probe so that the probe is less cumbersome and can be lightweight and small in diameter for ease of use and to minimize damage to the meat sample.

Against this background, the present invention was developed.

SUMMARY OF THE INVENTION
(DISCLOSURE OF THE INVENTION)

The invention relates to an apparatus and method for ascertaining and locating the boundary surface between a layer of fatty tissue and lean tissue in a cut of meat, such as beef, particularly large slabs of meet undergoing trimming and cutting in commercial meet processing facilitates. The invention exploits the fact that fatty tissue and lean tissue have significantly different responses to incident light energy. By gauging the degree to which a generated beam of light is scattered and reflected by the tissues under evaluation the invention permits the character of the tissue to be ascertained. An incident beam of light, such as green light, is generated and transmitted to a probe tip, which tip is inserted into the cut of meat under investigation. The light beam is emitted into the meat tissues from the probe tip, and then is scattered and reflected by the tissues, whereupon some fraction of the emitted light returns to the probe tip. The returning light energy is transmitted to a detector; relative changes in the returning light transmitted to the detector permit the operator to determine when the probe tip is approaching or penetrating the fat/lean tissue interface.

Thus, there is provided according to the invention a method for determining the location of the interface between fat and lean tissue in a cut of meat, comprising the steps of inserting a probe tip progressively into the cut, emitting light from the probe tip and into the cut, and monitoring the light returning to the tip from the cut. Monitoring the returning light preferably comprises monitoring for a decrease in returning light, and may comprise the additional step of correlating the amount of returned light with the physical location of the probe tip. The probe tip preferably comprises a generally frusto-conical probe tip having a point, to facilitate insertion of the probe tip into the meat being evaluated.

The step of inserting a probe tip preferably comprises the steps of defining in the probe tip a reception aperture and at least one emission aperture, generating light at a light source, providing a light detector, transmitting incident light from the light source to the at least one emission aperture, and transmitting reflected light from the reception aperture to the light detector. The step of defining a reception aperture may comprise locating the reception aperture at the central axis of the probe tip, whereas defining at least one emission aperture may comprise locating a plurality of emission apertures in an array around the reception aperture. The step of generating light optionally comprises selecting a light source from among the group consisting of light-emitting diodes and lasers, and selecting a light source preferably comprises selecting a source of green light. Transmitting incident light preferably comprises disposing optical fiber between the light source and the at least one emission aperture, and transmitting reflected light preferably comprises disposing optical fiber between the reception aperture and the light detector.

In a preferred method according to the invention, the step of inserting a probe tip comprises the steps of defining in the probe tip an aperture, generating light at a light source, providing a light detector, disposing a beam-splitter, transmitting incident light from the light source to the aperture via the beam splitter, and transmitting returning light from the aperture to the light detector via the beam splitter.

The step of inserting a probe tip may comprise inserting a plurality of probes.

A similar alternative method for determining the location of the interface between fat and lean tissue in a cut of meat is disclosed. The alternative method comprises the steps of inserting a probe tip progressively into the cut, determining the physical location of the probe tip, emitting light from the probe tip and into the cut, monitoring the light returning to the tip from the cut, and correlating the amount of returning light with the physical location of the probe tip. Monitoring the returning light preferably comprises monitoring for a decrease in returning light.

The step of inserting a probe tip preferably comprises providing a sharp probe tip having a conical portion tapering toward a point. Further, inserting a probe tip preferably comprises the steps of defining in the probe tip a reception aperture and at least one emission aperture, generating light at a light source remotely from the tip, providing a light detector remotely from the tip, transmitting incident light from the light source to the at least one emission aperture, and transmitting returning light from the reception aperture to the light detector. The step of defining a reception aperture may comprise locating the reception aperture at the central axis of and on the point of the probe tip, while defining at least one emission aperture may comprise locating a plurality of emission apertures in the conical portion of the tip in an array around the reception aperture.

A primary object of the present invention is to determine the fat/lean interface in meat tissue with minimal impact or damage to the meat tissue.

A primary advantage of the present invention is that optical fibers are used to both transmit light into, and receive the reflected light from, the meat tissue. The use of optical fibers allows the optical source and detector to be placed remotely from the probe so that the probe can be of small dimensions. Another advantage of the present invention is that the design and small size of the probe will enable automation of many manual operations in the meat industry. Yet another advantage of the present invention is that fat trimming operations can be automated due to the ability to locate the fat/lean interface in the cut of meat.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DESCRIPTION OF THE PREFERRED
EMBODIMENTS (BEST MODES FOR
CARRYING OUT THE INVENTION)

The present invention is a method and apparatus for determining the location of the interface between fat and lean meat in a cut of meat. The invention has a variety of potential applications, but it is contemplated that the invention will be especially beneficial in the context of automated trimming of fat. By the invention, mechanized devices or robotics may be employed to trim a desired amount of fat off a piece of meat, leaving thereon a certain thickness of fat. The present invention is not keyed to determining the quantitative thickness of an upper layer of fat; reflectance off the top of the fatty layer makes accurately finding the top of the fat very difficult, so the resulting thickness measurements may be inaccurate. For the purpose of locating the fat/lean interface, however, it does not matter if the fat thickness is indeterminate; it only matters that the location of the fat/lean interface is reasonably accurately determined, relative to a known datum, to permit cutting tools to be guided to some specified distance above the interface during automated trimming.

The inventive probe delivers light and returns reflected light via fiber optics. Electronic evaluation of the reflected light permits the operator to determine when the distal tip of the probe is immediately adjacent to the fat/lean interface in a cut of raw meat. Advantageously, the light emitter (preferably a laser) and the receiver need not be mounted in the probe itself, permitting the probe to have a desirably small overall diameter (just adequate to encase the optical fibers). The preferred embodiment of the probe tip apparatus features one receiving optical fiber at the center axis of the probe; alternative embodiments plausibly may include a bundle of two or more central receiving fibers, although one is strongly preferred to minimize the size of the probe tip. At least one, preferably three or four, emitting fibers are adjacent to the central receiving fiber. Most preferably, the three or four emitter fibers are disposed equidistantly around the central receiver fiber.

The tip of the inventive probe is advantageously sharp, with the emitter fibers located on the taper of the probe tip, and the receiving fiber located at the point. Thus, the precise point is as small in diameter as the receiving fiber. The relatively sharp probe tip is desirable, as there are tough membranes throughout a piece of meat. If a probe deforms the piece of meat (instead of "punching" though) when the probe tip encounters a membrane, measurement error will result. Accordingly the smaller the diameter of the central receiving fiber, generally the more accurately the interface location may be determined. As a practical matter, the probe apparatus minimum diameter is limited mainly by the light energy that must be transmitted down the emitter fibers and returned back up the receiving fiber for delivery to the detector.

Referring now to FIGS. 1 through 4, a probe tip 10 according to the invention for detecting the location of the fat/lean interface 44 is depicted. Probe tip 10 is mounted at the distal end of a tubular probe body 30, within which body are housed the optical fibers of the apparatus. Probe tip 10 and probe body 30 have a small diameter, preferably about 0.125 inches, such that penetration of the probe avoids damaging the meat. Probe tip 10 has a sharp point 12 to easily penetrate tissues.

The point 12 of probe tip 10 is frusto-conical in shape and contains an array of emission apertures 14, 14', 14" around the axis of the tip to release emitted light 24, 24', 24" (FIG. 1) coming from optical fibers contained within the probe. A central reception aperture 16 in point 12 admits reflected light 26 (FIG. 1) scattered and reflected from the tissue, which received light is conducted through the probe body 30 to a detector 18. (See FIG. 4.) While three emission apertures 14, 14', 14" are shown (best seen in FIG. 2C) in a symmetrical array around the probe tip 10, it is to be understood that a larger number of emission apertures 14 may be used without departing from the principles of the invention.

Figures 1, 2A, 2B, 2C:
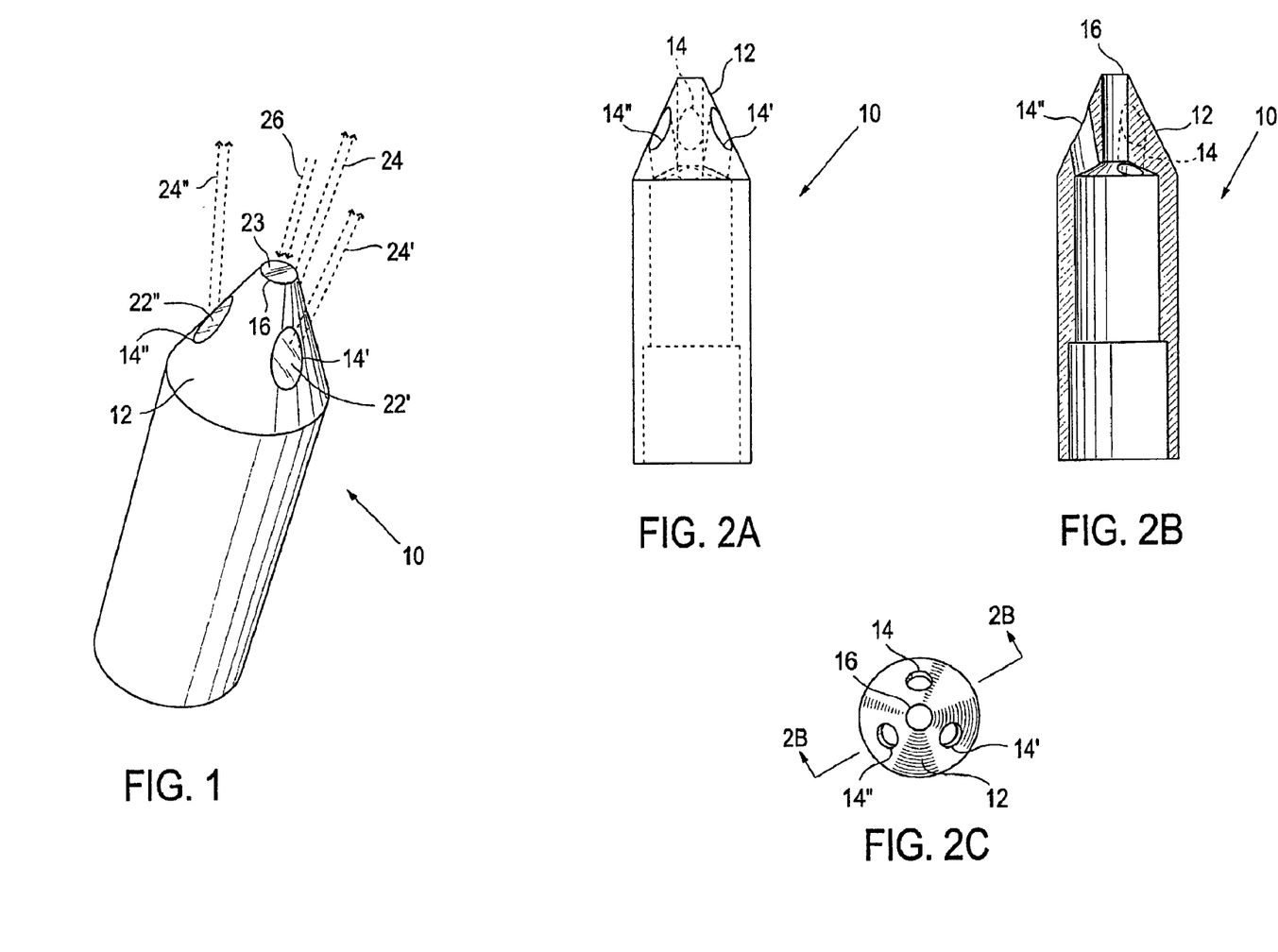
FIG. 1 is a perspective view of a probe tip according to the present invention.
FIG. 2A is a side view of the probe tip shown in FIG. 1.
FIG. 2B is a cross-sectional view of the probe tip seen in FIG. 2A, rotated by about 45°.
FIG. 2C is a top view of the probe tip shown in FIG. 1, showing the apertures for light transmission into the sample and the aperture for receipt of scattered light from the sample.
Figure 3:
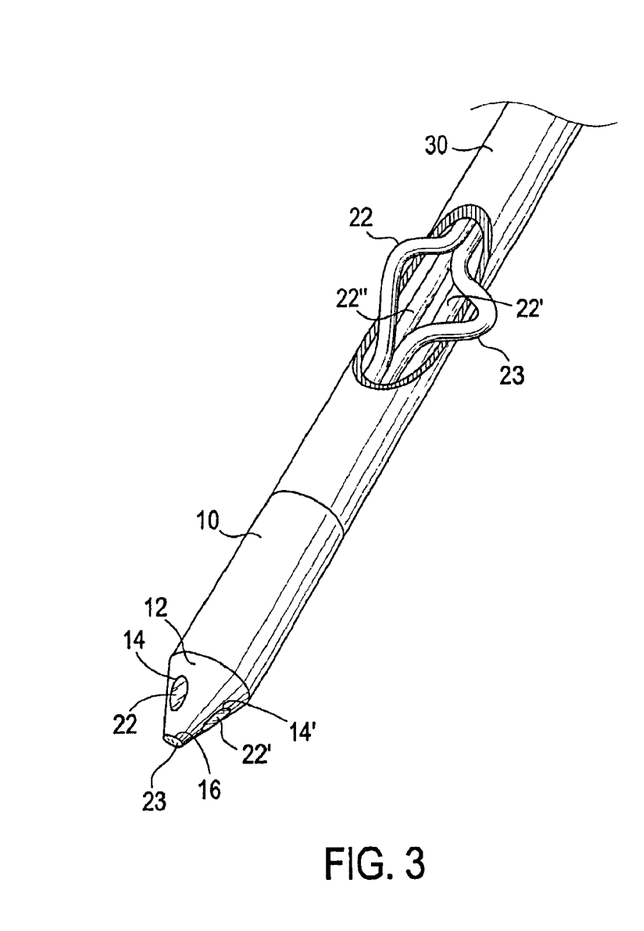
FIG. 3 is a perspective view of a probe body according to the invention attached to the probe tip of FIG. 1.
Figure 4:
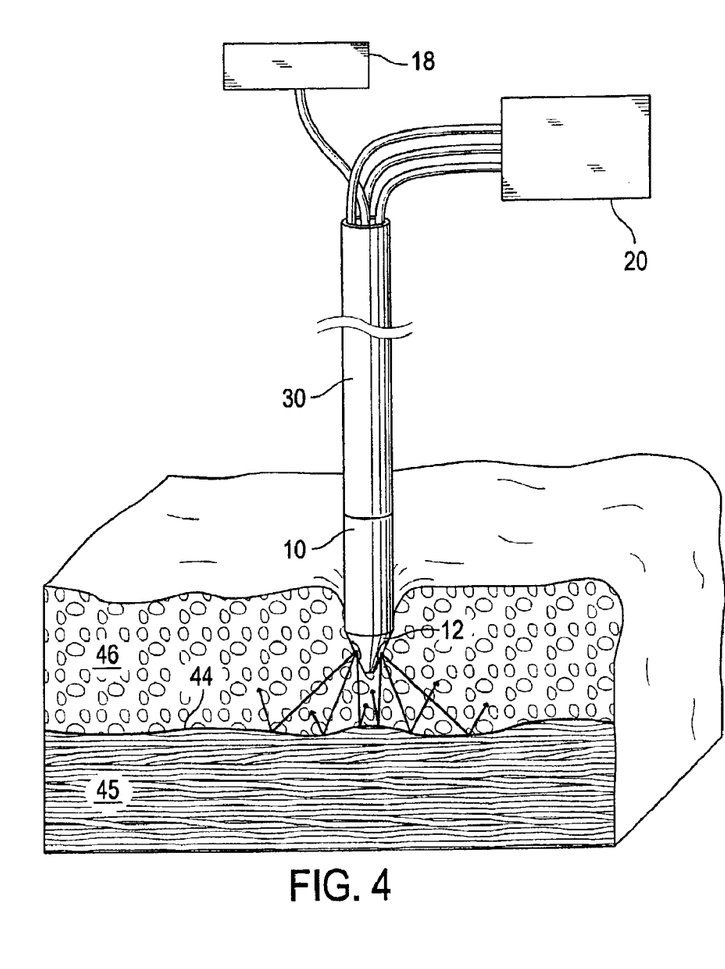
FIG. 4 is a diagram of the light source, probe tip, and detector of the present invention measuring a sample of tissue.

Three optical fibers 22, 22', 22" (only two shown in FIG. 1) of known construction are positioned longitudinally through the probe body 30 and into probe tip 10, such that light transmitted through each fiber is emitted (as indicated by directional arrows 24, 24', 24") out a respective one of the emission apertures 14, 14', 14". As seen in FIG. 1, each optical transmission fiber 22, 22', 22" is cut at an oblique angle at its distal end to align the end with its associated aperture 14, so to be flush or continuous with the contour of the outer surface of the frusto-conical point 12. Each of apertures 14, 14', 14" is of a dimension adequate for the distal end of the associated transmission fiber 22, 22', 22' to be friction-fit into the aperture and for light to be transmitted through the aperture. By way of non-limiting example, a relatively larger diameter probe, overall, may incorporate 1 mm diameter fibers. More preferably, optical fiber diameters of about 0.5 mm to about 0.75 mm diameter may be mounted. Fibers having a 0.25 mm diameter or less are alternatively acceptable, but may require a comparatively higher-powered laser light source. Optical fibers suitable for use in the invention include unjacketed Communications Grade Fibers, such as those available off-the-shelf from Edmund Scientific (Edmund Industrial Optics), Stock Number K02-542 (0.5 mm dia) and K02-543 (0.75 mm dia.).

Probe tip 10 features a reception aperture 16 at the distal end of the point 12. A receiving central optical fiber 23 is located axially in the center (i.e. on the axis) of probe tip 10, and terminates at the apex of point 12 in the reception aperture 16, as seen in FIGS. 2B and 2C. Green light emitted from light source 20, preferably about 532 nm in wavelength, is conducted through the three transmitting optical fibers 22, 22', 22" that terminate in the three respective apertures 14, 14', 14" in tip 10. Scattered and reflected green light 26 is received through aperture 16, and is transmitted through the receiving central optical fiber to detector 18. Central reception aperture 16 is of a diameter preferably in the range of about 0.25 mm to about 0.75 cm, so that the terminating end of the receiving fiber 23 can be friction-fit into aperture 16, and that light can be collected in the central aperture for transmission back into the probe body 30 via the receiving fiber 23.

Both the laser light source 20 and detector 18 are located remotely from the probe tip 10 or body 30. This remote location of light source 20 and detector 18 makes it possible for the probe to be of a very small diameter. The small diameter, preferably in the range of about 0.09375 inch to about 0.125 inch, results in little or no marring of the meat by the probe.

The outer diameters of the probe body 30 and the probe tip 10 preferably are approximately equal. The inventive tip 10 is a fabricated element, and the body 30 is a length of rigid tubing (e.g. stainless steel, 0.125 inch outside diameter). The tip 10, being fabricated especially for the inventive apparatus, has a wall thickness sufficiently thin such that there is just adequate room in the tip to house the fibers 22, 22', 22" and 23 (e.g., three emitting fibers and one receiving fiber).

Thus, in one suitable embodiment, the complete probe itself is approximately 8–12 inches long, and the fabricated tip 10 is approximately 0.50 inch long. The tip 10 of the probe is mounted, for example, approximately 6 inches above the conveyor belt upon which rests the meat to be tested. The probe undergoes controlled reciprocal, up-and-down movement through a distance of about 5.5 inches. Comparatively thicker cuts of meat (i.e. those bearing sizeable layers of fat) require a longer probe, although probes of increased overall length may require a concomitantly larger diameter 30 to prevent buckling. Similarly, relatively shorter probes may be employed on thinner pieces of meat.

The central receiver fiber 23 leads to an industrial fiber optic photo-detector 18. A suitable detector is the Digi-Key, Active Photodiode, FB120-ND. The analog signal output by the detector 18 then is run through an op-amp circuit to increase the current of the signal, prior to the signal being conducted to a data acquisition unit. The op-amp circuit optionally can be used to amplify the signal itself.

Light that is scattered and reflected back into the reception aperture 16, through the receiving fiber 23, and detected by detector 18 provides an indication of the type of tissue that point 12 of the probe tip 10 has encountered; generally, as the fat/lean interface 44 is approached by the probe tip 10, the light energy received by the receiving fiber 23 decreases, as increased light energy is absorbed by the lean meat 45. By mechanically driving the probe into the sample and measuring the returned light signal from the sample, the position of the fat/lean interface 44 within the meat sample can be determined. The absolute physical depth of the probe itself is monitored with a conventional linear displacement transducer.

In the preferred practice of the invention, the probe monitors for a decrease in returned light energy, as the probe tip penetrates fatty tissue and approaches lean tissue. It is noted, however, that a central aspect of the invention is the monitoring of relative changes in returned light energy, regardless whether the changes be decreases or increases. Accordingly, it is within the scope of the invention to monitor an approach to the lean/fat interface by a probe penetrating the lean tissue, in which instance the returning light energy is monitored for an abrupt increase in returned energy. (The lean tissue absorbs more light energy than the fat.)

The invention thus exploits the difference in the wavelengths of light that are transmitted and reflected by fatty tissue 46 and lean meat 44. Fat 46 is essentially white, and therefore transmits practically all colors. Lean 44 is essentially red, and thus absorbs all colors except red and reflects red. In the preferred embodiment, a green laser light source was employed, although it will be immediately understood that an apparatus according to the invention may employ other colors of light except red. In one preferred embodiment, a green LED supplying light at about 532 nm wavelength is usefully employed. Green LEDs are higher power and more readily available than blue LEDs, and thus are a preferred light source, especially in apparatuses incorporating very fine optical fibers ($\leq 0.25$ mm) which require higher powered light sources. Ordinary red (e.g. helium-neon, or ruby) lasers are not used in the invention, but lasers of nearly any other type may be employed as a light source.

Further, one of ordinary skill in the art will immediately appreciate that the number of emitting fibers and the number of receiving fibers in a particular probe is not critical. Various versions of the invention may employ from one to six or more emitting fibers, and from one to six or more receiving fibers, as indicated by specific applications of the invention.

One or more probes according to the invention can be incorporated into a robotic system to permit gauging of the fat/lean interface and automated trimming along a commercial meat processing line. In one possible application, for example, a series of pieces of meat to be tested are moved along a processing line by a conveyor belt. The conveyor moves at a continuous speed, so that some meat pieces can be "probed" while other pieces concurrently are being trimmed at a location further "down the line." In such a preferred application, a bank of probes, for example a five-by-ten rectangular array of 50 probes according to the invention, is deployed. As a particular piece of meat passes by on the conveyor, the bank of probes descends into probing contact with that piece. While the bank of probes is evaluating a piece, the bank temporarily attaches to the conveyor, or is otherwise driven to move at the same speed and direction of the meat, so to probe the entire piece while it moves along. Once the piece has been probed, the bank of probes is withdrawn from the meat and moved back to its "ready" position to await the arrival of the next piece to be tested. The use of an array of probes permits the creation of a 3-D "map" of the fat/lean interface, or more specifically, of the height of the lean tissue (e.g. distance above the conveyor or other datum). The map may feature information generated by interpolating data between the specific probe points, to generate a digital contour of the interface.

A map of the lean meat surface at the interface is useful for further "downline" processing. A map of lean meat height (as the cut leaves the trimming zone of the processing line) permits lean cut portion control later on the line. For example, a 3-D map of meat height can be integrated to obtain the area of the lean surface, and the operators thus know exactly at what thickness to chuck out the lean to obtain portions of a selected size or weight. Knowing the lean density would allow for automated cutting of 12- or 16-ounce steaks, for example.

In an alternative embodiment, a plurality of probes (e.g., three to ten probes) according to the invention are mounted in a row above a conventional conveyor, such as a conveyor belt. A piece of meat to be tested is placed on the belt. When the meat is under the row of probes, the conveyor belt stops; a signal is sent to actuate the probes and perform the evaluation to determine the location of the fat/lean interface. After the test is completed, the probes are retracted, and the conveyor belt renews movement. After the conveyor belt has moved a specified predetermined distance, it stops again, and the signal is sent to again actuate the probes. The process is repeated as many times as specified by the operator. As in the preferred embodiment, a map of the fat/lean interface may be generated with respect to some predetermined datum (such as the horizontal conveyor surface). The periodic starting and stopping of the conveyor in this version reduces the overall time efficiency of the process (which may be undesirable in high-volume commercial operations).

In still another alternative, a single row of probes travels with the conveyor but also travels relative to the piece of meat to be evaluated. The row of probes descends and retracts while traveling parallel to the conveyor and at the same speed, so that relative to the piece (which is moving along with the conveyor) the probes are descending and retracting straight up and down. In such an application, when the row of probes is in a retracted position, it briefly stops moving at all, to let the meat progress a predetermined distance farther on the conveyor, the probes are then actuated to descend into contact with the piece and to retract again, while moving at conveyor speed.

One of ordinary skill in the art of robotics will immediately appreciate that there thus are a variety of modes of employing the inventive probe in an automated system to map the lean height or the fat/lean interface. The entire process can be automated to permit repeated tests on a particular piece of meat without stopping the conveyor or slowing down the system.

Nevertheless, in the simplest version, one probe, or a plurality of probes disposed in a single row, may be actuated to move straight up and down with respect to a stationary piece of meat. Between each actuation, the position of the probe or row of probes is incrementally adjusted to provide a "survey" of the entire piece of meat over a horizontal plane. The detected points of fat/lean interface provide a digital approximation of the contour of the interface, which contour is communicated to an automated fat trimmer further down the processing line.

In yet another alternative embodiment of the inventive probe according to the invention, a single optical fiber is used within the probe, rather than two or more separate optical fibers. The single optical fiber embodiment of the probe is easier to manufacture. It also is smaller in size, and thus less destructive to the tissues under analysis. There is, however, a compromise in the form of an increase in the amount of light lost from the system. In this embodiment, a single optical fiber both emits the incident beam as well as receives the scattered light from the tissue sample. Beam splitting optics are used to divert the reflected light coming up through the fiber into the detector.

Figure 6:
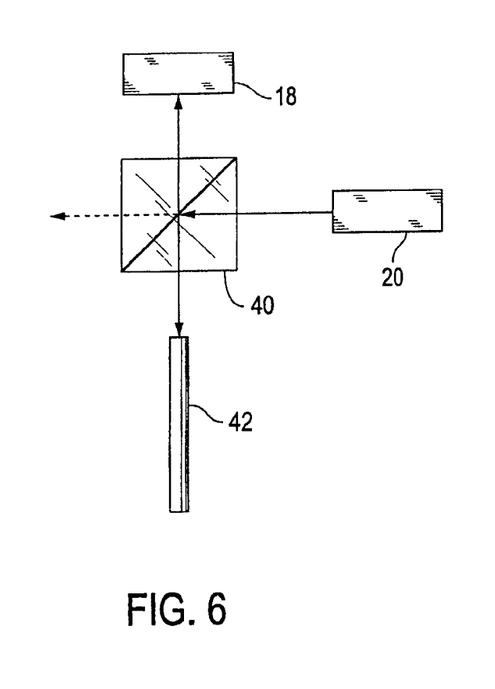
FIG. 6 is a diagram depicting the fundamental arrangement of a "split-beam" single-fiber alternative embodiment of the invention.

FIG. 6 illustrates this alternative embodiment, and shows the overall relationships among of the fundamental components, with simple lines indicating the light paths. The apparatus uses a beam splitter 40, of conventional construction, to allow the scattered and reflected light from the sample to reach the photodetector 18, so that both the incident transmitted light and the reflected received light can travel through the single fiber 42.

Figure 7A:
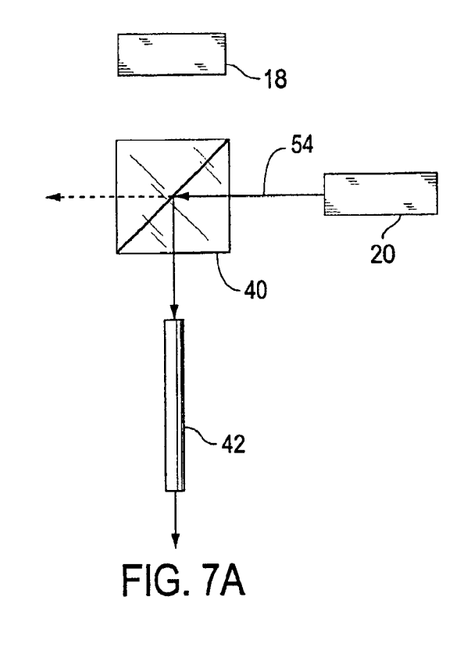
FIG. 7A is a diagram depicting the paths of the incident light beam rays of the embodiment illustrated by FIG. 6.
Figure 7B:
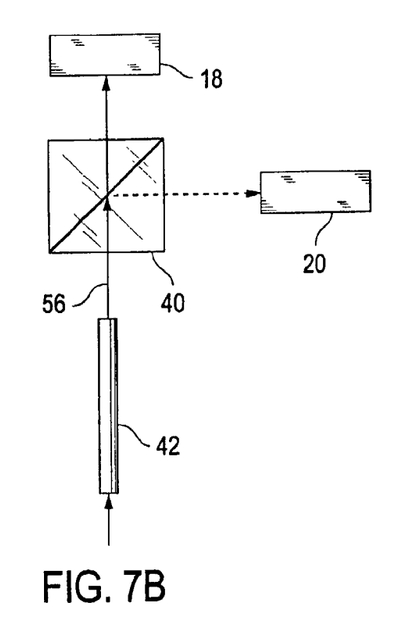
FIG. 7B is a diagram depicting the paths of the reflected light beam rays of the embodiment illustrated by FIG. 6.

FIGS. 7A and 7B show the transmitted and return light rays, respectively. In this embodiment, the beam splitter 40 is a cemented cube with a half-silvered interface. About half the emitted incident beam 54 is reflected down into the single fiber 42 within the probe tip (not shown), and the other half of the emitted beam passes straight through the beam splitter 40 and is lost. The return or received beam 56 is similarly affected, in that 50 percent of the return beam energy is transmitted through the beam splitter 40 and into the detector 18, while the other half is reflected back toward the light source 20, such as a laser. These sequential losses of about 50 percent each means that the ultimate signal to the detector 18 is only one-quarter as strong as it otherwise would be. Further, the fiber 42 itself is imperfect, resulting in some backscatter of the light transmitted by the fiber. Since the return signal is relatively weak, this backscatter makes discrimination more difficult. Nevertheless, this alternative embodiment, permitting an emitted beam and a received beam to be simultaneously or alternately conveyed within a single fiber 42, promotes a reduction in the overall diameter of the probe tip 10 and body 30.

Figure 5:
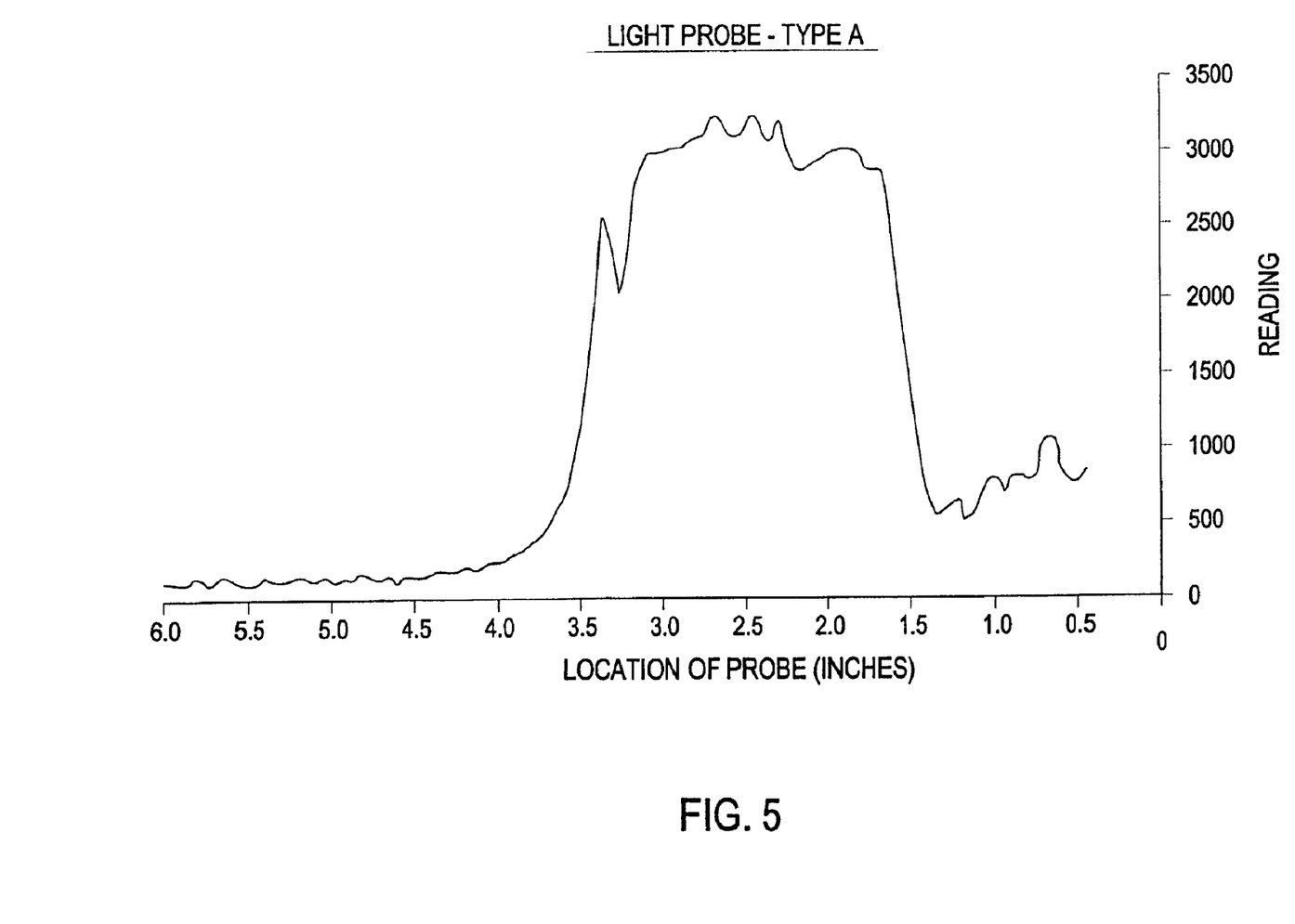
FIG. 5 is a graph depicting the light intensity reading versus the probe location in an experimental sample. In the figure, on the x-axis is the measured location of the tip of the probe, and on the y-axis is the return from the receiver proportional to the amount of light being received.

Further understanding of the invention is provided by the graph of FIG. 5. The detector sends a voltage or current signal to a data acquisition device, such as a computer processor or meter, which can generate a graph such as that depicted in the figure. In FIG. 5, data acquisition "counts" are shown on the y-axis ("Reading" scale) of the graph. The counts need not be converted to quantified volts or amps; the absolute count value is non-critical, since relative changes in value convey the necessary data regarding the fat/lean interface. The relative physical location of the probe tip is given on the x-axis.

In the particular case illustrated in FIG. 5, the probe started with the probe tip at a height of 6 inches, and then began moving downward toward the interface. Simultaneous readings were taken from the light receiver-detector and a displacement transducer measuring the probe's physical location. The probe moved continuously down to a final height (in this example, about 0.5 inches), and readings were continuously taken and stored. The "top" of the piece of meat (that is, the uppermost surface of the sample being evaluated, which surface is defined by fatty tissue) was located at about 3.5 inches above datum. (The invention is not intended to locate the "top" with specific accuracy.) The fat/lean interface location, with respect to datum, corresponded to the point on the graph where a drastic drop in reflected light occurs (fat reflects green light, lean meat absorbs it) at approximately 1.5 inches.

Thus, the data reduction and analysis technique of the invention is straightforward. The operator or computer processor simply monitors or the received signal to exceed a threshold, indicating that the probe has entered fat. The signal then is continuously monitored, as the probe progressively penetrates the sample. A subsequent decrease (usually abrupt) in the signal below a second predetermined threshold indicates that the probe tip is at or in lean tissue; at that instant, the probe's height measurement (e.g., from the x-axis in FIG. 5) corresponding to the breach of the second threshold is logged for later use in fat trimming, etc.

Industrial Applicability

The invention is further illustrated by the following non-limiting examples.

EXAMPLE 1

A first optical probe design was investigated for determining the fat/lean interface in a tissue sample. Two types of light sources were investigated: an infinite light beam of green laser light (532 nm wavelength) and green LED light. The amount of returned, scattered or reflected light at the tip of the probe indicated the material properties of the sample at the point where the probe tip was inserted into the sample. As lean muscle absorbs much more green light than fat, the point of the fat/lean interface was determined using the amount of returned light in addition to the depth of insertion of the probe.

The optical probe consisted of a thin and pointed metal probe mounted on a linear stage. Fiber optic cables down the center of the probe transmitted light from a source and received light back from the sample to be input into the detector. The first light source used in this example was a Class 3a lasers (<5 mW) having a 532 nm wavelength. The second light source tested was green LEDs, being less expensive and safer than other light sources. However, green LEDs supply comparatively less light energy, and thus may generate less accurate readings. In this example, fiber optic LEDs from Digi-Key®, PN FB127-ND, 60 mW, 530 nm wavelength were utilized. It is to be understood that the inventive probe can be designed with LEDs as the light source, provided they supply sufficient output power.

The body of the probe was designed of 0.125 inch outside diameter stainless steel tubing (thin walled). Two fiber optic cables were arranged longitudinally through the interior of the tube. The first optical fiber cable transmitted light into the tissue sample, and the second fiber optic cable received the scattered light returned from the tissue sample. Data retrieved using this probe is depicted in FIG. 5.

FIG. 5 is a plot showing the optical readings obtained with respect to the location of the probe depth in inches into the tissue sample. The depth of insertion is represented by the abscissa and the optical reading shown by the detector is indicated on the ordinate. As previously explained, the reading is simply "counts" from the data acquisition system. One could convert the counts to voltage, but the absolute value is not critical, as the method of the invention seeks to detect abrupt changes in value. FIG. 5 illustrates that the detector reading is very low when the probe is in the air, abruptly increases as the probe moves into fatty tissue, and then abruptly decreases when the fat/lean interface is encountered.

One difficulty encountered with certain initial probe designs was the inability of the probe tip to penetrate tissue membranes without significantly deforming the sample. This difficulty was attributed to found to be due to the probe tip being too dull. An additional problem with dull or overly oblique tip designs is the possibility for fat to be pushed by the probe into the meat tissue, thereby compromising readings. Therefore, a series of probes with sharper tips were designed and tested. The angle between the axis of the probe tip and the tapered conical surface thereof preferably is less than about 40°. Again, sharper points are better for penetrating tissue without deforming it, but sharper probe tips are more expensive to make and may deflect reflected light away from the receiver aperture.

EXAMPLE 2

A second probe was tested which consisted of a 0.125 inch diameter probe body and tip having four 0.03-inch diameter optical fibers arranged longitudinally along the tube interior. Three of the optical fibers were used to transmit the light into the tissue sample and terminated at the tapered portion of the probe tip at respective apertures within the probe tip to provide light into the sample. The fourth of the optical fibers received scattered light from the sample and was positioned at the central axis of the probe tip and terminated flush at an aperture at the point of the probe tip, as shown in FIG. 1.

Tests were conducted using both green laser light as well as green LEDs as the light source. Tests revealed a large, distinct, and easily-measurable difference in optical response between fat and lean tissue in samples when using the green laser as the light source. Results obtained using the green LEDs were less accurate. The use of LEDs showed significant noise and reduced difference in optical response (compared to the response from a laser light source) between fat and lean tissue. However, in instances of degraded response from LED sources, the fat/lean interface may be found through the use of data processing algorithms prepared using laser sources—i.e. data obtained with an LED required sophisticated data reduction and filtering and more testing to ensure reliable and accurate results.

Using the green laser as the light source in the optical probe, a simple algorithm was developed to automatically determine the location of the fat/lean interface. For most meat samples tested, the error associated with the probe was within 0.125 inch. In approximately 20% of the test samples, the samples contained a tough membrane at the fat/lean interface and resulted in an error of approximately 0.25 inch.

EXAMPLE 3

To improve the performance on those samples containing tough membranes at the fat/lean interface, a third probe was designed that incorporated a 0.009-inch (0.25 mm) diameter center receiving optical fiber in place of the 0.03-inch (0.75 mm) receiving optical fiber used in Examples 1 and 2. The smaller center fiber made it possible for the probe tip to be sharper. A difficulty encountered with the smaller center return fiber was that a smaller amount of light was collected and, in some instances, did not gather sufficient light to generate a usable return signal. From this and other experiments, it has been determined that the center return optical fiber is preferably in the range of 0.5 mm to about 0.75 mm in diameter.

EXAMPLE 4

On an exemplary prototype "probing station," the probe design of Example 2 was incorporated into a machine that could map the fat/lean interface on an entire piece of meat. Nine probes were mounted above a conveyor belt, lined up at 2-inch intervals, perpendicular to the motion of the conveyor. The probes were mounted on a bracket connected to pneumatic cylinders. The pneumatic cylinders could be actuated from a computer control system via relays to solenoid valves. A cable-type linear displacement transducer (UniMeasure LX Series) was attached to the bracket, and the device thus could measure the location and motion of the probes. Green lasers (one for each probe) and receiver circuit boards were mounted on the frame, the length of fiber was such that the probes could move down and up relative to the lasers/boards (i.e. there was "slack" in the fiber line.) The optical fibers were encased in a TEFLON sheath to protect them during probe movement.

The probes on this prototype "probing station" did not render as accurate results as those obtained in the lab. The fibers were a lot longer, had more bends and were moving around, resulting in significant light losses. Nevertheless, correlative measurements yielded sufficient data to indicate that multi-probe stations merit further development according to the fundamental principles of the invention.

The preceding examples can be repeated with similar success by substituting the generically or specifically described operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method for determining the location of the interface between fat and lean tissue in a cut of meat, comprising the steps of:

providing a generally frusto-conical probe tip having a point;

defining in the probe tip a reception aperture and at least one emission aperture, the reception aperture being located at the central axis of the probe tip;

locating a light detector remotely from the probe tip;

inserting the probe tip progressively into the cut;

originating light at a source located remotely from the probe tip;

transmitting incident light from the source to the at least one emission aperture in the probe tip via optical fiber;

emitting light from the probe tip and into the cut;

transmitting reflected light from the reception aperture through optical fiber to the light detector; and monitoring the light returning to the tip from the cut.

2. A method according to claim 1 wherein monitoring the returning light comprises monitoring for a decrease in returning light.

3. A method according to claim 2 comprising the additional step of correlating the amount of returned light with the physical location of the probe tip.

4. A method according to claim 1 wherein defining at least one emission aperture comprises locating a plurality of emission apertures in an array around the reception aperture.

5. A method according to claim 1 wherein the step of originating light comprises selecting a light source from among the group consisting of light-emitting diodes and lasers.

6. A method according to claim 5 wherein selecting a light source comprises selecting a source of green light.

7. A method according to claim 1 wherein the step of transmitting incident light comprises disposing the optical fiber between the light source and the at least one emission aperture.

8. A method according to claim 1 wherein transmitting reflected light comprises disposing optical fiber between the reception aperture and the light detector.

9. A method according to claim 1 wherein the step of inserting a probe tip comprises the steps of:

defining in the probe tip an aperture;

providing a light detector;

disposing a beam-splitter;

transmitting incident light from the light source to the aperture via the beam splitter; and transmitting returning light from the aperture to the light detector via the beam splitter.

10. A method according to claim 1 wherein the step of inserting a probe tip comprises inserting a plurality of probes.

11. A method for determining the location of the interface between fat and lean tissue in a cut of meat, comprising the steps of:

providing a sharp probe tip having a conical portion tapering toward a point;

defining in the probe tip a reception aperture and at least one emission aperture, the reception aperture being located on the central axis of and on the point of the probe tip;

providing a light detector remotely from the tip;

inserting the probe tip progressively into the cut;

determining the physical location of the probe tip;

transmitting incident light from a light source located remotely from the probe, through optical fiber, to the at least one emission aperture;

emitting light from the probe tip and into the cut;

transmitting returning light from the reception aperture through optical fiber to the light detector;

monitoring the light returning to the tip from the cut; and correlating the amount of returning light with the physical location of the probe tip.

12. A method according to claim 11 wherein monitoring the returning light comprises monitoring for a decrease in returning light.

13. A method according to claim 11 wherein defining at least one emission aperture comprises locating a plurality of emission apertures in the conical portion of the tip in an array around the reception aperture.

14. A method according to claim 13 wherein the step of generating light comprises selecting a light source from among the group consisting of light-emitting diodes and lasers.

15. A method according to claim 14 wherein selecting a light source comprises selecting a source of green light.

16. A method according to claim 15 wherein transmitting incident light comprises disposing optical fiber between the light source and the at least one emission aperture, and wherein transmitting reflected light comprises disposing optical fiber between the reception aperture and the light detector.

17. A method according to claim 11 wherein the step of inserting a probe tip comprises inserting a plurality of probes.

18. A method for determining the location of the interface between fat and lean tissue in a cut of meat, comprising the steps of:

providing a sharp probe tip having a conical portion tapering toward a point;

defining in the probe tip a reception aperture and at least one emission aperture;

inserting the probe tip progressively into the cut;

determining the physical location of the probe tip;

emitting light from the probe tip and into the cut, the light being originated at a source remote from the probe;

monitoring the light returning to the tip from the cut; and correlating the amount of returning light with the physical location of the probe tip;

wherein defining a reception aperture comprises locating the reception aperture at the central axis of and on the point of the probe tip.

* * * * *